US00PP12917P2

(12) United States Plant Patent
Utecht

(10) Patent No.: US PP12,917 P2
(45) Date of Patent: Sep. 3, 2002

(54) GERANIUM PLANT NAMED 'FISRORED'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,003

(22) Filed: Jan. 31, 2001

(51) Int. Cl.[7] ..... A01H 5/00
(52) U.S. Cl. ..... Plt./330
(58) Field of Search ..... Plt./330, 328

(56) References Cited

PUBLICATIONS

German Application for 'FISRORED' Sep. 15, 1998.
German Denomination for 'FISRORED' Aug. 15, 1999.
*Plant Varieties Journal*, No. 38, Jan. 2001, p. 52 (Canada).
European Community Application—'FISRORED' (Oct. 15, 1999).
European Community Denomination—'FISRORED' (Oct. 15, 1999).
European Community Grant—'FISRORED' (#6819) (Feb. 15, 2001).
Fischer USA 2000/2001 Catalogue.
GTITM UPOVROM Citation for 'FISRORED' as per QZ PBR 991051; Jul. 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrored', as described and illustrated, and particularly characterized by the combined features of deep red, semi-double flowers, large, many-flowered umbels, foliage with strong zonation, vigorous growth and moderately tall plant habit, and medium (mid season) begin of flowering.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisrored'.

'Fisrored' is a product of a planned breeding program which had the objective of creating new geranium varieties with deep red flower color.

'Fisrored' originated from a hybridization made by the inventor Angelika Utecht in a controlled breeding program in Galdar, Gran Canaria, Spain, in 1994.

The female parent was a hybrid seedling, no. 1477-2 (unpatented), having intense red, single-type flowers, large inflorescences, large, dark-green leaves and medium plant habit. The male parent of 'Fisrored' was the variety 'Fistador', U.S. plant patent applied for Ser. No. 09/323,149, which is characterized by scarlet semi-double flowers, zoned foliage, and medium-tall, round plant habit.

'Fisrored' was selected as one flowering plant within the progeny of the stated cross by Angelika Utecht in 1995 in a controlled environment in Galdar, Gran Canaria, Spain. The first act of asexual reproduction of 'Fisrored' was accomplished when vegetative cuttings were taken from the initial selection in the fall of 1995 in a controlled environment in Galdar, Gran Canaria, Spain, by, or under the supervision of, Angelika Utecht.

Horticultural examination of plants grown from cuttings of the plant initiated in May 1997 in Hillscheid, Federal Republic of Germany, and continuing thereafter, has demonstrated that the combination of characteristics as herein disclosed for 'Fisrored' are firmly fixed and are retained through successive generations of asexual reproduction.

'Fisrored' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisrored' in combination distinguish this geranium as a new and distinct cultivar:

1. Deep red (true red) flower color, semi-double, round flowers;
2. Large inflorescences with many flowers, tightly arranged;
3. Medium-green foliage with strong zonation;
4. Vigorous growth, and relatively tall, bushy plant habit; and
5. mid season spring flowering response.

Of the many commercial cultivars known to the present inventor, the most similar in comparison to 'Fisrored' is the parental variety 'Fistador'. In comparison to 'Fistador', 'Fisrored' has a similar flower color, longer peduncles and larger inflorescence, and considerably taller plant habit, making it more suitable for extensive outdoor planting.

BRIEF DESCRIPTION OF THE DRAWING

The accompanying photographic drawing shows typical flower and foliage characteristics of 'Fisrored' with colors being as true as possible with an illustration of this type.

The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart (R.H.S). The color values were determined indoors from plants developed in a green-house in May, 2000, in Hillscheid, Germany.

Classification:

*Botanical.*—A hybrid of the species *Pelargonium zonale* L'Hérit.

*Commercial.*—Zonal geranium, cv. 'Fisrored'.

Inflorescence:

*Umbel.*—Shape: Slightly flattened and wide, nearly semi-spherical. Average diameter: 117 mm. Average depth: 60–65 mm. Peduncle length: 148 mm. Peduncle color: Grass-green, RHS 143 A. Pedicel length: 34 mm. Pedicel color: Reddish RHS 181 A on the lower part; dark red RHS 60 A on the upper part. Number of flowers per umbel: About 40. Lastingness of the umbel: Approximately 18 days at 18° C.

*Corolla.*—Average diameter: 43 mm. Form: Semi-double. Shape: Small to medium-sized, round, cup-shaped. Number of petals: 7–9. Size of petals: Upper petals are 21–22 mm long, 19–21 mm wide. Lower petals are 21–23 mm long, 21–23 mm wide. Shape of petals: Obovate, upper end weakly rounded, attenuate base, margin entire. Number of petaloids: 1–2. Color of petaloids: Lower surface RHS 43 B, upper surface RHS 43 A. Color (general tonality from a distance of three meters): Intense medium red. Color of upper petals: From RHS 43 A to RHS 45 B. Markings of upper petals: Weak dark-red veins, RHS 46 A. Color of lower petals: Between RHS 43 A and 45 B, no markings. Color of lower surface of petals: Between RHS 43 A and RHS 43 B. Color of sepals: Lower surface light green RHS 143 A, base reddish-brown, RHS 179 A; upper surface light green, RHS 143 C, base reddish-brown RHS 179 A. Number of sepals: 5. Size of sepals: 10–11 mm in length, 5 mm in width for the largest upper sepal; 2–3 mm in diameter for the other sepals. Shape of sepals: Linear to lanceolate, acute tip, truncate base, margin entire, surface with weak pubescence.

*Bud: (just prior to petals unfolding).*—Shape: Elliptical. Color (lower part — sepals): Mainly green, RHS 137 D, some infusion of anthocyanin RHS 179 B at the base. Color (upper part — petals): Orange-red, RHS 43 A. Length: 15 mm. Width: 9 mm.

*Reproductive organs.*—Androecium: About 5 fertile anthers, whitish to pink filaments, yellow-orange pollen RHS 30 A, moderate quantity of pollen produced. Gynoecium: 5–6-lobed stigma, whitish filament, one pistil per flower. Fertility/seed set: Occasionally a few seeds are developed, oblong in shape, brown RHS 177 B.

*Spring flowering response period.*—In Hillscheid, Germany, in 2000, plants had on average 0.8 flowers opened 8 weeks after planting of rooted cuttings.

*Outdoor flower production.*—Medium number of inflorescences, the flower count in 2000, in Hillscheid, Germany, indicated about 3–4 inflorescences per plant in mid-May.

*Durability.*—Good stability of flower color, relatively good rain resistance. Lastingness of the individual bloom: Approximately 8 days at 18° C.

*Fragrance.*—None.

Plant:

*Foliage.*—Form: Kidney-shaped, with open base. Margin: Bicrenated. Apex: Rounded, with weak lobes. Base: Open, cordate with open gap between lower ends of leaf. Size of leaf: 97 mm wide, 60–65 mm long. Texture: Slightly velvety, short pubescence. Color of upper surface: Medium-green, approximately RHS 137 B. Color of zonation: Strong, brown, about RHS 166 A.

*General appearance and form.*—Stem color: Green, RHS 143 A. Internode length: 10–20 mm. Branching pattern: 5.8 branches. Plant size: 23.5 cm, as measured from the base of the stem (soil surface) to the surface of the foliage canopy, without inflorescences, 36.5 cm wide.

*Disease/pest resistance/susceptibility.*—None observed to date.

I claim:

1. A new and distinct cultivar of geranium plant named 'Fisrored', as described and illustrated.

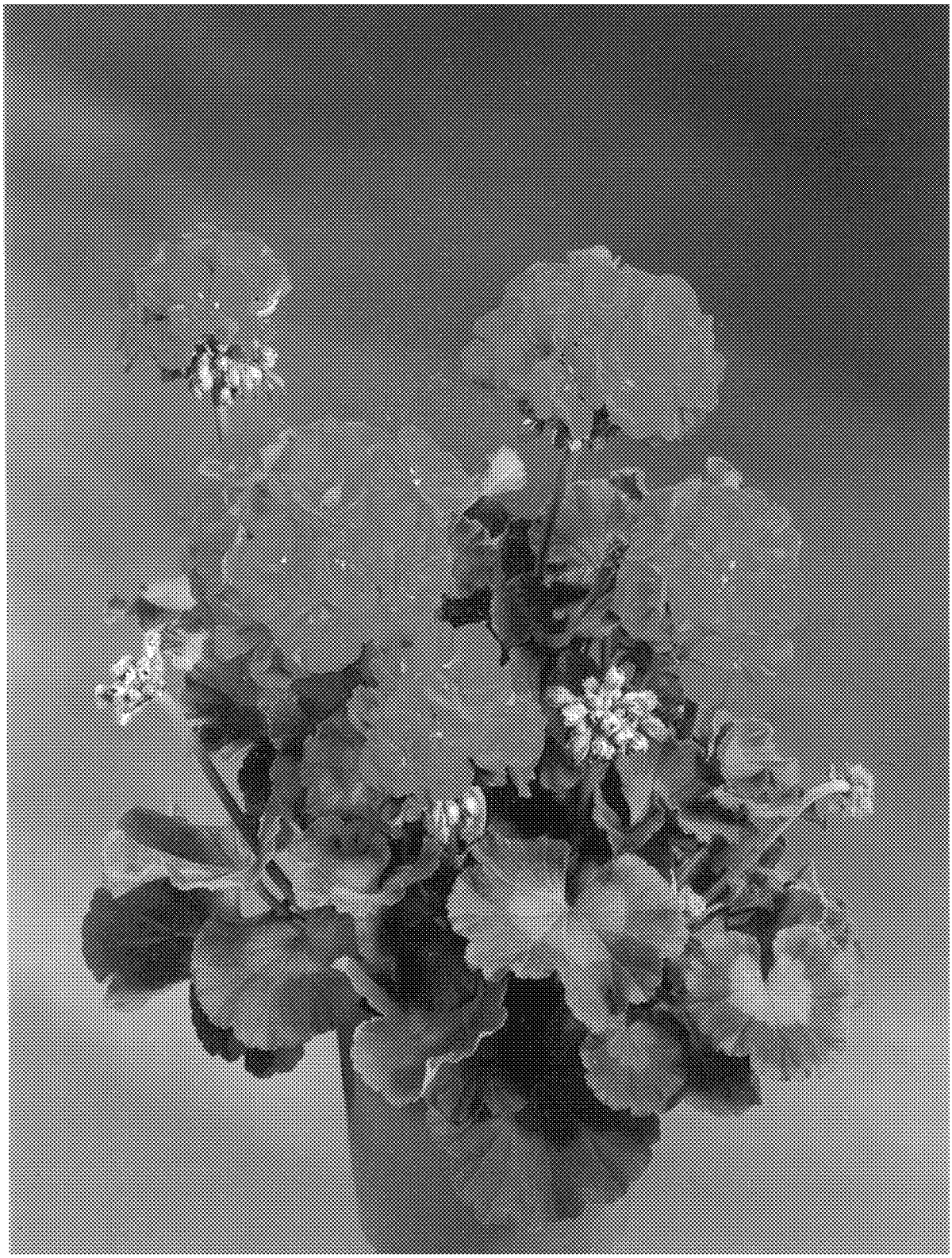

* * * * *